United States Patent
Dupuis et al.

(10) Patent No.: US 6,468,549 B1
(45) Date of Patent: *Oct. 22, 2002

(54) ACIDIC COMPOSITIONS OR DERMATOLOGICAL COMPOSITION CONTAINING A CROSSLINKED POLY (2-ACRYLAMIDO-2-METHYLPROPANESULFONIC ACID) NEUTRALIZED TO AT LEAST 90%

(75) Inventors: Christine Dupuis; Isabelle Hansenne, both of Paris; Mirelle Maubru, Chatou; Laurence Sebillote-Arnaud, Les Roses; Raluca Lorant, Thiais, all of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/885,167

(22) Filed: Jun. 30, 1997

(30) Foreign Application Priority Data

Jun. 28, 1996 (FR) ............................................. 96 08108

(51) Int. Cl.$^7$ ............................ A61K 7/04; A61K 7/16; A61K 7/42; A61K 7/48
(52) U.S. Cl. ........................ 424/401; 424/56; 424/59; 424/61; 424/70.11; 424/70.17; 514/772.3; 514/844; 514/880
(58) Field of Search .................. 424/401, 59, 70.1, 424/56, 61, 63, 64, 65, 69, 70.5, 70.6, 70.8, 70.9, 70.11, 70.17, 74; 252/302; 514/844, 880, 936, 772.3, 845, 846, 847, 848, 881, 942

(56) References Cited

U.S. PATENT DOCUMENTS

| | | | | |
|---|---|---|---|---|
| 3,931,089 A | | 1/1976 | Karl ........................ 260/29.65 |
| 5,114,706 A | | 5/1992 | Duvel ........................ 424/70 |
| 5,531,993 A | * | 7/1996 | Griat ........................ 424/401 |
| 5,679,328 A | | 10/1997 | Dupuis .................... 424/70.13 |
| 5,879,718 A | * | 3/1999 | Sebillote-Arnaud ......... 424/705 |
| 5,891,452 A | * | 4/1999 | Sebillote-Arnaud et al. ..... 424/401 |
| 5,908,618 A | * | 6/1999 | Lorant ...................... 424/70.5 |
| 5,952,395 A | * | 9/1999 | Lorant .................... 514/772.4 |
| 5,993,832 A | * | 11/1999 | Lorant et al. ............... 424/401 |
| 6,120,780 A | * | 9/2000 | Dupuis et al. .............. 424/401 |
| 6,123,960 A | * | 9/2000 | Faure et al. ................ 424/450 |
| 6,180,118 B1 | * | 1/2001 | Maubru ...................... 424/401 |
| 6,287,543 B1 | * | 9/2001 | Terren et al. ................. 424/64 |

FOREIGN PATENT DOCUMENTS

EP 0 680 748 11/1995

OTHER PUBLICATIONS

Dupuis, *Chemical Abstracts*, vol. 121, #286350, 1995.*

* cited by examiner

Primary Examiner—Jeffrey E. Russell
(74) Attorney, Agent, or Firm—Finnegan, Henderson, Farabow, Garrett & Dunner, L.L.P.

(57) ABSTRACT

The invention relates to a cosmetic or dermatological composition containing an acidic aqueous medium and at least one crosslinked poly(2-acrylamido-2-methylpropanesulfonic acid) polymer neutralized to at least 90%. The composition contains, distributed randomly:

(a) from 90 to 99.9% by weight of units of formula (1); and

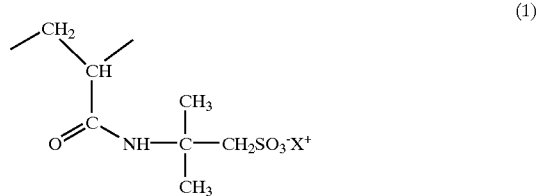
(1)

in which $X^+$ denotes a cation or a mixture of cations, it being possible for at most 10 mol % of the cations $X^+$ to be protons $H^+$;

(b) from 0.01 to 10% by weight of crosslinking units originating from at least one monomer having at least two olefinic double bonds; the proportions by weight being defined with respect to the total weight of the polymer. The invention also relates to the use of this composition in the cosmetic treatment of keratinous substances, in particular of the skin, hair and mucous membranes, and in particular to a non-therapeutic process for depigmentation of the skin.

33 Claims, No Drawings

ACIDIC COMPOSITIONS OR DERMATOLOGICAL COMPOSITION CONTAINING A CROSSLINKED POLY (2-ACRYLAMIDO-2-METHYLPROPANESULFONIC ACID) NEUTRALIZED TO AT LEAST 90%

The invention relates to a cosmetic or dermatological composition containing an acidic aqueous medium and at least one crosslinked poly(2-acrylamido-2-methylpropanesulphonic acid) polymer which is neutralized to at least 90%.

The invention also relates to the use of this composition in the cosmetic treatment of keratinous substances, in particular of the skin, hair and mucous membranes, in particular to a non-therapeutic process for depigmentation of the skin.

At different periods in their life, some people witness the appearance on the skin, and more particularly on the hands, of darker or more highly colored blemishes which give the skin a heterogeneous appearance. These blemishes are generally due to significant production of melanin in the epidermis or the dermis of the skin.

These blemishes can be related to a number of phenomena and more especially to aging. In some cases, these blemishes can become cancerous. It is consequently increasingly sought to decrease, indeed remove, these blemishes. Use is made of organic active principles, such as kojic acid, caffeic acid or salicylic acid and its derivatives, in treating these blemishes.

Damaged hair can also be treated with compositions based on acidic active principles, in order to tone it up, to restore its vigor and to strengthen the keratinous fibers.

Compositions conventionally used in the cosmetic or dermatological fields are water-in-oil (W/O) emulsions, oil-in-water (O/W) emulsions or aqueous gels in which it is often difficult, indeed even impossible, to incorporate organic acid active principles, such as kojic acid, caffeic acid or salicylic acid and its derivatives.

These acidic active principles generally have a tendency to recrystallize or to degrade. This results in a more or less significant loss in effectiveness of these compositions, according to the degree of recrystallization or degradation, which goes against the desired objective. In addition, this recrystallization or degradation can modify the overall stability of these compositions as well as their appearance, which can dissuade the user from employing these specific treatment compositions.

The use is known, in dissolving some of these active principles, of W/O or O/W emulsions in which the aqueous phase exhibits an acidic pH. For these emulsions to be stable (non separation of the aqueous and oily phases), it is necessary to use emulsifiers (or surfactants). Unfortunately, these surfactants are often irritating to the skin. In addition, these emulsions often lack freshness on application, which can interfere with their uses during warm periods of the year or in hot countries. An aqueous gel is much more appreciated under these conditions of use. However, its very large amount of water does not allow active principles exhibiting a degree of lipophilic nature to be introduced therein. Moreover, the stability of these gels is mediocre.

The need thus remains for a stable composition having the appearance of a gel, which can be used in particular in the cosmetic or dermatological fields, Which makes possible sufficient solubilization of the acidic a-active principles generally used in these fields for the purpose of maximum effectiveness.

With this objective, the use has already been envisaged, in European Patent Application EP-A-680,748, of acidic compositions in the gel form containing crosslinked cationic copolymers or homopolymers which are substantially soluble in aqueous media, and in particular in water, and which are composed of units resulting from the reaction between (i) a cationic monomer containing ethylenic unsaturation or a cationic mixture of monomers containing ethylenic unsaturation and (ii) a crosslinking agent containing ethylenic polyunsaturation. These gelling agents make it possible to stabilize and to dissolve these acidic active principles in compositions containing aqueous media rich in organic solvent.

The use has also already been envisaged, in European Patent Application EP-A-642,781, as gelling and stabilizing agents, of a crosslinked anionic copolymer which is substantially soluble in water and which is composed of units deriving from the reaction between (i) acrylamide, (ii) 2-acrylamido-2-methylpropanesulphonic acid and (iii) at least one compound containing olefinic polyunsaturation (crosslinking agent) in acidic oil-in-water emulsions containing acidic organic active principles.

These two polymer families exhibit the disadvantage, however, of not allowing the production of spontaneously transparent gels, which is harmful to the aesthetic appearance of the final product. Moreover, in the presence of certain acidic organic active principles, such as glycolic acid, these polymers lose their thickening or gelling power and do not allow formulations of high and stable viscosity to be obtained.

The inventors have discovered, surprisingly, a new family of thickening or gelling polymers allowing acidic cosmetic and dermatological formulations to be obtained in the form of transparent and homogeneous gels making it possible to attain high viscosities which are stable over time at room temperature or at higher temperatures.

Moreover, these polymers make it possible to dissolve and stabilize acidic organicactive principles in a cosmetic or dermatological composition containing an acidic aqueous medium at pH values of less than or equal to 5.

In particular, they make it possible to dissolve and to stabilize organic acid active principles in a cosmetic or dermatological composition containing an acidic aqueous medium rich in organic solvent. Compositions containing an aqueous medium rich in organic solvent is understood to mean a composition containing at least 45% by weight of organic solvent with respect to the total weight of the composition.

Finally, these polymers make it possible to produce gels which are transparent, non-runny, non-stringy, soft and smooth on application.

Thus, a subject of the invention is a cosmetic or dermatological composition containing a cosmetically acceptable acidic aqueous medium and at least one crosslinked poly(2-acrylamido-2-methyl-propanesulphonic acid) polymer neutralized to at least 90%.

The composition of the invention has a certain consistency or behavior; it is not stringy, i.e., it does not form strings when taken with the finger. It is more preferably provided in the form of a gel.

The pH of the aqueous medium is advantageously less than or equal to 5 and in practice preferably in the range from 1 to 4. Above the pH value of 6, the formulation no longer exhibits difficulties.

The crosslinked and virtually or completely neutralized poly(2-acrylamido-2-methylpropanesulphonic acid) polymers in accordance with the invention are water-soluble or swellable in water. They are in general characterized in that they comprise, distributed randomly:

(a) from 90 to 99.9% by weight of units of the following formula (1):

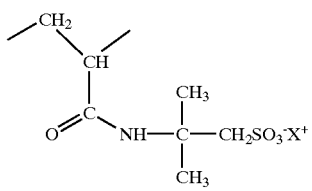
(1)

in which $X^+$ denotes a cation or a mixture of cations, it being possible for at most 10 mol % of the cations $X^+$ to be protons $H^+$; and (b) from 0.01 to 10% by weight of crosslinking units originating from at least one monomer having at least two olefinic double bonds; the proportions by weight being defined with respect to the total weight of the polymer.

The polymers of the invention preferentially contain a number of units of formula (1) in an amount which is sufficiently high to obtain a hydrodynamic volume of the polymer, in solution in water, having a radius ranging from 10 to 500 nm, with a homogeneous and unimodal distribution.

The more particularly preferred polymers according to the invention comprise from 98 to 99.5% by weight of units of formula (1) and from 0.2 to 2% by weight of crosslinking units.

$X^+$ represents a cation or a mixture of cations selected in particular from a proton, an alkali metal cation, a cation equivalent to that of an alkaline-earth metal or the ammonium ion. More particularly, 90 to 100 mol % of the cations are $NH_4^+$ cations and 0 to 10 mol % are protons ($H^+$).

The crosslinking monomers having at least two olefinic double bonds are selected, for example, from dipropylene glycol diallyl ether, polyglycol diallyl ethers, triethylene glycol divinyl ether, hydroquinone diallyl ether, tetrallyloxenthanoyl or other allyl or vinyl ethers polyfunctional alcohols, tetraethylene glycol diacrylate, triallylamine, trimethylolpropane diallyl ether, methylenebisacrylamide or divinylbenzene.

The crosslinking monomers having at least two olefinic double bonds are more particularly selected from those corresponding to the following formula (2):

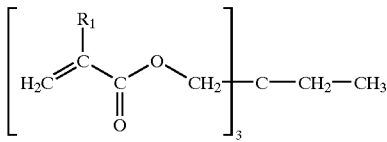
(2)

in which $R_1$ denotes a hydrogen atom or a $C_1$–$C_4$ alkyl. The crosslinking monomer is preferably methyl (trimethylolpropane triacrylate).

The polymerization reaction of the polymers of the invention produces not only linear chains but also branched or crosslinked molecules of polymer. These molecules can be characterized in particular by their rheological behavior in water but more particularly by dynamic light scattering.

In the case of the characterization of the molecules by dynamic light scattering, the distribution of the hydrodynamic volume of the structures of the polymer is measured. Macromolecules dissolved in water are flexible and surrounded by a solvation envelope formed from water molecules. With charged polymers, such as those of the invention, the size of the molecules depends on the amount of salt in the water. In polar solvents, the uniform charge along the main chain of the polymer results in a significant expansion in the polymerchain. The fact of increasing the amount of salt increases the amount of electrolyte in the solvent and screens the uniform charges of the polymer. In addition to the molecules transported in the solvation envelope, solvent molecules are fixed in the cavities of the polymer. In this case, the solvent molecules form part of the dissolved macromolecules and move at the same average speed. Thus, the hydrodynamic volume describes the linear dimension of the macromolecule and of these solvation molecules.

The hydrodynamic volume $v_h$ is determined by the following formula:

$$v_h = M/N_A \times (V_2 + dV_1)$$

with:

M denoting the mass in grams of the undissolved macromolecule;

$N_A$ denoting Avogadro's number;

$V_1$ denoting the specific volume of the solvent;

$V_2$ denoting the specific volume of the macromolecule;

d denoting the mass in grams of the solvent which is associated with 1 gram of undissolved macromolecule.

If the hydrodynamic particle is spherical, it is then easy to calculate the hydrodynamic radius from the hydrodynamic volume by the formula:

$$V_h = 4\pi R^3/3$$

with R denoting the hydrodynamic radius.

Cases where hydrodynamic particles are perfect spheres are extremely rare. The majority of synthetic polymers involve compacted structures or ellipsoids of high eccentricity. In this case, the radius is determined with respect to a sphere which is equivalent from a frictional viewpoint to the shape of the particle under consideration.

As a general rule, the determination is carried out with respect to molecular weight distributions and thus with respect to hydrodynamic radius and volume distributions. For polydispersed systems, the distribution of the diffusion coefficients must be calculated. From this distribution, the results relating to the radial distribution and to the distribution of the hydrodynamic volumes is deduced therefrom.

The hydrodynamic volumes of the polymers of the invention are in particular determined by dynamic light scattering from the Stokes-Einstein diffusion coefficients D of formula: $D = kT/6\pi\eta R$ where k is Boltzmann's constant, T is the absolute temperature in degrees Kelvin, $\eta$ is the viscosity of the solvent (water) and R is the hydrodynamic radius.

These diffusion coefficients D are measured according to the method of characterization of a mixture of polymers by laser scattering described in the following references:

(1) Pecora, R; Dynamic Light Scattering; Plenum Press, New York, 1976;

(2) Chu B; Dynamic Light Scattering; Academic Press, New York, 1994;

(3) Schmitz, K S; Introduction to Dynamic Light Scattering; Academic Press, New York, 1990;

(4) Provincher S. W.; Comp. Phys., 27, 213,1982;

(5) Provincher S. W.; Comp. Phys., 27, 229,1982;

(6) ALV Laservertriebgesellschaft mhH, Robert Bosch Str. 47, D-63225 Langen, Germany;

(7) ELS-Reinheimer Strasse 11, D-64846 Gross-Zimmern, Germany; and (8) Chi Wu et al., Macromolecules, 1995, 28,4914–4919.

The particularly preferred polymers are those exhibiting a viscosity, measured with a Brookfield viscometer in a 2% solution in water at 25° C., of greater than or equal to 1000 cPs, preferably ranging from 5000 to 40,000 cPs and more preferably ranging from 6500 to 35,000 cPs.

The at least one crosslinked poly(2-acrylamido-2-methylpropanesulphonic acid) polymer of the invention can be obtained according to the preparation process comprising the following stages:

(a) the 2-acrylamido-2-methylpropanesulphonic acid monomer is dispersed or dissolved in the free form in a tert-butanol or water and tert-butanol solution;

(b) the solution or the dispersion of MPSA monomer obtained in (a) is neutralized with one or a number of inorganic or organic bases, preferably ammonia $NH_3$, in an amount which makes it possible to obtain a degree of neutralization of the sulphonic acid functional groups of the polymer ranging from 90 to 100%;

(c) the crosslinking monomer or monomers is/are added to the solution or dispersion obtained in (b); and (d) a conventional radical polymerization is carried out in the presence of free radical initiators at a temperature ranging from 10 to 150° C., the polymer precipitating in the solution or dispersion based on tert-butanol.

The at least one virtually or completely neutralized crosslinked poly(2-acrylamido-2-methylpropanesulphonic acid) polymer is present in the cosmetic or dermatological compositions of the invention in concentrations preferably ranging from 0.01 to 20% by weight with respect to the total weight of the composition and more preferably from 0.1 to 10% by weight.

The compositions according to the invention can contain cosmetic or dermatological acidic organic active principles dissolved and stabilized in the acidic aqueous medium, in the presence of at least one crosslinked poly(2-acrylamido-2-methylpropanesulphonic acid) polymer as defined above.

Mention may be made, as organic acid active principles which can be dissolved in the composition of the invention, of ascorbic acid, kojic acid, citric acid, caffeic acid, salicylic acid and its derivatives (for example, 5-n-octanoyl- or 5-decanoylsalicylic acid), α-hydroxy acids, such as lactic acid, methyllactic acid, glucuronic acid, glycolic acid, pyruvic acid, 2-hydroxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytetradecanoic acid, 2-hydroxyhexadecanoic acid, 2-hydroxyoctadecanoic acid, 2-hydroxytetracosanoic acid or 2-hydroxyeicosanoic acid, mandelic acid, benzoic acid, phenyllactic acid, gluconic acid, galacturonic acid, citric acid, aleuritic acid, ribonic acid, tartronic acid, tartaric acid, malic acid, fumaric acid, retinoic acid and its derivatives, benzene-1,4-di(3-methylidene-10-camphorsulphonic acid), urocanic acid, 2-phenylbenzimidazole-5-sulphonic acid, α-(2-oxo-3-bornylidene)toluene4-sulphonic acid or 2-hydroxy4-methoxy-5-sulphonic acid. It is also possible to use any natural or synthetic compound containing such acids, such as plant extracts and more especially fruit extracts. It is also possible to dissolve acidic xanthine derivatives (caffeine, theophylline), β-glycyrrhetinic acid or asiatic acid.

The compositions of the invention contain a cosmetically acceptable aqueous medium, i.e., a medium compatible with all keratinous substances, such as the skin, nails, mucous membranes and hair, or any other cutaneous region of the body.

The cosmetically or dermatologically acceptable medium of the compositions according to the invention is more particularly composed of water and optionally of cosmetically or dermatologically acceptable organic solvents.

The organic solvents can represent from 5% to 98% of the total weight of the composition. They can be selected from hydrophilic organic solvents, lipophilic organic solvents, amphiphilic solvents and their mixtures.

Mention may be made, among hydrophilic organic solvents, for example, of linear or branched lower monoalcohols having from 1 to 8 carbon atoms, such as ethanol, propanol, butanol, isopropanol or isobutanol; polyethylene glycols having from 6 to 80 ethylene oxide units; polyols, such as propylene glycol, isoprene glycol, butylene glycol, glycerol or sorbitol; mono- or dialkyl isosorbides in which the alkyl groups have from 1 to 5 carbon atoms, such as dimethyl isosorbide; or glycol ethers, such as diethylene glycol monomethyl or monoethyl ether and propylene glycol ethers, such as dipropylene glycol methyl ether.

Mention may be made, as amphiphilic organic solvents, of polyols, such as polypropylene glycol (PPG) derivatives, for example esters of polypropylene glycol and of fatty acid or ethers of PPG and of fatty alcohol, such as PPG-23 oleyl ether and PPG-36 oleate.

Mention may be made, as lipophilic organic solvents, for example, of fatty esters, such as diisopropyl adipate or dioctyl adipate, or alkyl benzoates.

In order for the cosmetic or dermatological compositions of the invention to be more pleasant to use, i.e., softer on application, more nourishing, and more emollient, it is possible to add a fatty phase to the medium of these compositions.

The fatty phase preferably represents from 0% to 50% of the total weight of the composition. This fatty phase can contain one or a number of oils preferably selected from:

water-soluble or liposoluble, organomodified or non-organomodified, linear, branched or cyclic, volatile or non-volatile silicones;

mineral oils, such as liquid paraffin or liquid petrolatum;

oils of animal origin, such as perhydrosqualene;

oils of plant origin, such as sweet almond oil, avocado oil, castor oil, olive oil, jojoba oil, sesame oil, groundnut oil, macadamia oil, grape seed oil, rapeseed oil or coconut oil;

synthetic oils, such as purcellin oil or isoparaffins;

fluorinated and perfluorinated oils; and esters of fatty acids, such as purcellin oil.

The fatty phase can also contain, as fatty substance, one or a number of fatty alcohols, fatty acids such as stearic acid or waxes such as paraffin wax, polyethylene waxes, carnauba wax and beeswax.

The compositions of the invention can contain adjuvants usual in the cosmetic and dermatological fields: other conventional hydrophilic or lipophilic gelling or thickening agents; hydrophilic or lipophilic active principles; preservatives; antioxidants; fragrances; emulsifiers; moisturizing agents; pigmenting agents; depigmenting agents; keratolytic agents; vitamins, emollients; sequestering agents; surfactants; polymers; basifying or acidifying agents; fillers; agents for combatting free radicals; ceramides; sunscreen agents, in particular ultraviolet screening agents; insect repellents; slimming agents; coloring materials; bactericides; or antidandruff agents. The amounts of these different adjuvants are those conventionally used in the fields under consideration.

Of course, the person skilled in the art will take care to choose the possible compound or compounds to be added to the composition according to the invention so that the advantageous properties intrinsically attached to the composition in accordance with the invention are not, or not substantially, detrimentally affected by the envisaged addition.

The compositions according to the invention can be provided in all the forms appropriate for a topical application, in particular in the form of solutions of the lotion or serum type, in the form of aqueous gels or in the form of emulsions obtained by dispersion of a fatty phase in an aqueous phase (O/W) or vice versa (W/O), with a liquid or semi-liquid consistency, such as milks, more or less smooth creams or pastes. These compositions are prepared according to the usual methods.

The compositions according to the invention can be used as rinse-out hair products or as leave-in hair products, in particular for washing, caring for, conditioning or form retention of the hairstyle or shaping keratinous fibers, such as the hair.

The inventive compositions can be styling products, such as hair setting lotions, blow-drying lotions or fixing and styling compositions. The lotions can be packaged in various forms, in particular in vaporizers or pump-action sprays or in aerosol containers, in order to provide for application of the composition in the vaporized form or in the foam form. Such packaging forms are indicated, for example, when it is desired to obtain a spray or a foam for fixing or treating the hair.

The compositions of the invention can also be shampoos or compositions of a rinse-out or leave-in nature to be applied before or after shampooing, dyeing, bleaching, perming or hair straightening.

The compositions of the invention can also be used as a care or hygiene product, such as protection, treatment or care creams for the face, for the hands or for the body, protection or care body milks or lotions, gels or foams for caring for the skin and mucous membranes or for cleansing the skin.

The compositions of the invention can also be used as anti-sun products.

The compositions can also consist of solid preparations constituting cleansing bars or soaps.

The compositions of the invention can also be used as oral care products, such as toothpastes.

The compositions can be make-up products.

Another subject of the invention is a process for the non-therapeutic cosmetic treatment of the skin, scalp, hair, eyelashes, eyebrows, nails or mucous membranes, characterized in that a composition as defined above is applied on the skin, scalp, hair, eyelashes, eyebrows, nails or mucous membranes according to the usual technique for the use of this composition. For example: application of creams, gels, serums, lotions or milks on the skin, scalp or mucous membranes. The type of treatment depends on the acidic active principle or principles dissolved in the composition.

More especially, the invention relates to a non-therapeutic process for depigmenting the skin of the human face or body which consists in applying a composition as defined above on the skin.

A further subject of the invention is the use of the above composition in preparing a pomade or an ointment intended for the therapeutic treatment of the human face or body, including the hands, in particular for treating acne and blackheads on greasy skins.

A further subject of the invention is the use of a polymer as defined above for gelling or thickening a cosmetic or dermatological composition containing an acidic aqueous medium.

A further subject of the invention is the use of a polymer as defined above for gelling or thickening a cosmetic or dermatological composition containing an aqueous medium rich in organic solvent.

A further subject of the invention is the use of a polymer as defined above for dissolving and stabilizing an organic acid active principle in a cosmetic or dermatological composition containing an acidic aqueous medium.

A further subject of the invention is the use of a polymer as defined above for dissolving and stabilizing an organic acid active principle in a cosmetic or dermatological composition containing an aqueous medium rich in organic solvent.

The following examples illustrate the invention without limiting it.

PREPARATION EXAMPLE A 2006.2. g of tert-butanol were introduced into a 5 liter round-bottomed flask equipped with a stirrer, a reflux condenser, a thermometer and a device for conveying nitrogen and ammonia, followed by the introduction of 340.0 g of 2-acrylamido-2-methylpropanesulphonic acid, which was dispersed in the solution with vigorous stirring. After 30 minutes, ammonia was added via the upper pipe of the round-bottomed flask and the reaction mixture was maintained for 30 minutes at room temperature until a pH of the order of 6–6.5 was obtained. 32.0 g of a 25% solution, of trimethylolpropane triacrylate in tert-butanol were then introduced and the reaction mixture was heated to 60° C. while simultaneously rendered inert by introduction of nitrogen into the round-bottomed flask. Once this temperature was reached, dilauroyl peroxide was added. The reaction began immediately, which was reflected by a rise in temperature and by precipitation of the polymerizate. 15 minutes after the polymerization began, a stream of nitrogen was introduced. 30 minutes after the addition of the initiator, the temperature of the reaction mixture reached a maximum of 65–70° C. 30 minutes after having reached this temperature, the reaction mixture was heated to reflux and was maintained under these conditions for 2 hours. The formation of a thick paste was observed during the reaction.

The reaction mixture was cooled to room temperature and the product obtained was filtered off. The recovered paste was then dried under vacuum at 60–70° C. for 24 hours. 391 g of crosslinked and neutralized poly(2-acrylamido-2-methylpropanesulphonic acid) were obtained with a viscosity, measured with a Brookfield viscometer, rotor 4, at a rotational speed of 100 revolutions/minute in a 2% solution in water at 25° C., ranging from 15,000 cPs to 35,000 cPs. The viscosity of the polymer may chosen and controlled according to conventional means, depending on the envisaged cosmetic application.

The hydrodynamic radius of the polymer obtained in an aqueous solution, determined by dynamic light scattering, was 440 nm.

PREPARATION EXAMPLE B 2006.2 g of tert-butanol were introduced into a 5 liter round-bottomed flask equipped with a stirrer, a reflux condenser, a thermometer and a device for conveying nitrogen and ammonia, followed by the introduction of 340.0 g of 2-acrylamido-2-methylpropanesulphonic acid, which was dispersed in the solution with vigorous stirring. After 30 minutes, ammonia was added via the upper pipe of the round-bottomed flask and the reaction mixture was maintained for 30 minutes at room temperature until a pH of the order of 6–6.5 was obtained. 19.2 g of a 25% solution of trimethylolpropane triacrylate in tert-butanol were then introduced and the reaction mixture was heated to 60° C. while simultaneously rendered inert by introduction of nitrogen into the round-bottomed flask. Once this temperature was reached, dilauroyl peroxide was added. The reaction began immediately, which was reflected by a rise in temperature and by precipitation of the polymerizate. 15 minutes after the polymerization began, a stream of nitrogen was introduced. 30 minutes after the addition of the initiator, the temperature of the reaction mixture reached a maximum of 65–70° C. 30 minutes after having reached this temperature, the reaction mixture was heated to reflux and maintained under these conditions for 2 hours. The formation of a thick paste was observed during the reaction.

The reaction mixture was cooled to room temperature and the product obtained was filtered off. The recovered paste was then dried under vacuum at 60–70° C. for 24 hours. 391 g of crosslinked and neutralized poly(2-acrylamido-2-methylpropanesulphonic acid) were obtained with a viscosity, measured with a Brookfield viscometer, rotor 4, at a rotational speed of 100 revolutions/minute in a 2% solution in water at 25° C., of the order of 7000 cPs.

The hydrodynamic radius of the polymer obtained in an aqueous solution, determined by dynamic light scattering, was 160 nm.

EXAMPLE 1
Shampoo

| | |
|---|---|
| Sodium lauryl ether sulphate, sold under the name of Empicol ESB3/FL by the company Albright and Wilson | 10 g AM |
| Crosslinked poly(2-acrylamido-2-methylpropanesulphonic acid) neutralized with ammonia, prepared according to the process of Preparation Example B, with a viscosity of the order of 17,000 cPs in a 2% solution in water at 25° C. | 1.5 g AM |
| Citric acid | 3 g |
| Water q.s. for | 100 g |
| pH adjusted to 4.8 (NaOH) | |

This shampoo had the appearance of a translucent, thickened, stable and homogeneous liquid. It had good foaming properties.

EXAMPLE 2
Transparent Anti-sun Gel

| | |
|---|---|
| Glycerol | 4 g |
| Crosslinked poly(2-acrylamido-2-methylpropanesulphonic acid) neutralized with ammonia, prepared according to the process of Preparation Example A, with a viscosity of the order of 16,000 cPs in a 2% solution in water at 25° C. | 1.0 g AM |
| Benzene-1,4-di(3-methylidene-10-camphorsulphonic acid) as a 33% aqueous solution | 6 g |
| Propylene glycol | 18 g |
| Sterilized demineralized water | 70 g |
| pH = 1.7 | |

A stable, thick, transparent, smooth and homogeneous gel was obtained.

EXAMPLE 3
Transparent Anti-mosquito Gel

| | |
|---|---|
| Glycerol | 4 g |
| Crosslinked poly(2-acrylamido-2-methylpropanesulphonic acid) neutralized with ammonia, prepared according to the process of Preparation Example A, with a viscosity of the order of 16,000 cPs in a 2% solution in water at 25° C. | 0.8 g AM |
| Ethyl N-butyl-N-acetylaminopropionate | 15 g |
| N,N-Diethyl-m-toluamide | 20 g |
| Propylene glycol | 18 g |
| 96° Ethanol | 23 g |
| Sterilized demineralized water | 19.2 g |
| pH = 3.95 | |

A stable, thick, transparent, smooth and homogeneous gel was obtained.

EXAMPLE 4
Anti-aging Gel

| | |
|---|---|
| Crosslinked poly(2-acrylamido-2-methylpropanesulphonic acid) neutralized with ammonia, prepared according to the process of Preparation Example B, with a viscosity of the order of 7000 cPs in a 2% solution in water at 25° C. | 2.0 g |
| Benzene-1,4-di(3-methylidene-10-camphorsulphonic acid) | 0.7 g |
| Lactic acid | 2 g |
| Glycerol | 3 g |
| Preservative q.s. | |
| Distilled water q.s. for | 100 g |
| pH = 3.5 | |

A stable, thick, transparent, smooth and homogeneous gel was obtained.

EXAMPLE 5
Depigmenting Gel

| | |
|---|---|
| Crosslinked poly(2-acrylamido-2-methylpropanesulphonic acid) neutralized with ammonia, prepared according to the process of Preparation Example B, with a viscosity of the order of 7000 cPs in a 2% solution in water at 25° C. | 2.0 g AM |
| Benzene-1,4-di(3-methylidene-10-camphorsulphonic acid) | 0.7 g |
| Kojic acid | 1 g |
| Dimethicone copolymer | 2 g |
| Preservative q.s. | |
| Distilled water q.s. for | 100 g |
| pH = 4.5 | |

A stable, moderately thick, transparent and homogeneous gel was obtained.

EXAMPLE 6
Keratolytic Gel

| | |
|---|---|
| Crosslinked poly(2-acrylamido-2-methylpropanesulphonic acid) neutralized with ammonia, prepared according to the process of Preparation Example B, with a viscosity of the order of 7000 cPs in a 2% solution in water at | 2.0 g AM |

-continued

| | |
|---|---|
| 25° C. | |
| Glycolic acid | 2 g |
| Dimethicone copolymer | 2 g |
| Preservative q.s. | |
| Distilled water q.s. for | 100 g |
| pH = 2 | |

A stable, transparent, smooth and homogeneous gel was obtained.

EXAMPLE 7

Shower Gel

| | |
|---|---|
| Crosslinked poly(2-acrylamido-2-methylpropanesulphonic acid) neutralized with ammonia, prepared according to the process of Preparation Example A, with a viscosity of the order of 16,000 cPs in a 2% solution in water at 25° C. | 1.2 g AM |
| Hydrogenated tallow myristyl glycol | 1 g |
| Sodium salt of methyl p-hydroxy-benzoate | 0.215 g |
| Disodium salt of ethylenediamine-tetraacetic acid | 0.26 g |
| Glycerol | 4 g |
| 50/50 Dimethyldiallylammonium chloride/acrylamide copolymer as an 8% aqueous solution | 0.5 g |
| 1,3-Dimethylol-5,5-dimethylhydantoin as a 55% aqueous solution | 0.172 g |
| Sodium lauryl ether sulphate containing 2.2 mol of ethylene oxide | 10 g |
| Triethanolamine lauryl sulphate as a 46% aqueous solution | 25 g |
| Cocoylbetaine as a 32% aqueous solution | 5 g |
| Fragrance | 0.15 g |
| HCl q.s. | pH 5.5 |
| Sterilized demineralized water | 100 g |

A stable, thick, moderately transparent, smooth and homogeneous gel was obtained.

EXAMPLE 8

Mouthwash

| | |
|---|---|
| Cross(inked poly(2-acrylamido-2-methyl-propanesulphonic acid) neutralized with ammonia, prepared according to the process of Preparation Example A, with a viscosity of the order of 16,000 cPs in a 2% solution in water at 25° C. | 0.1 g AM |
| Methyl p-hydroxybenzoate | 0.1 g |
| Glycerol | 5 g |
| Sorbitan monolaurate oxyethylenated with 20 mol of ethylene oxide | 0.4 g |
| Sodium lauryl sulphate powder | 0.25 g |
| Sodium fluoride | 0.05 g |
| 96° Ethanol | 5 g |
| Fragrance | 0.15 g |
| HCl q.s. | pH 5 |
| Sterilized demineralized water | 100 g |

This mouthwash had the appearance of a translucent, thickened, stable and homogeneous liquid.

EXAMPLE 9
Refreshing Moisturizing Gel

| | |
|---|---|
| Crosslinked poly(2-acrylamido-2-methylpropanesulphonic acid) neutralized with ammonia, prepared according to the process of Preparation Example B, with a viscosity of the order of 7000 cPs in a 2% solution in water at 25° C. | 2.0 g AM |
| 96° Ethyl alcohol | 20 g |
| Glycerol | 3 g |
| Distilled water q.s. for | 100 g |
| pH = 4.8 | |

A stable, transparent and homogeneous gel was obtained.

EXAMPLE 10
Depigmenting Cream (Oil-in-water Emulsion)

| | |
|---|---|
| Fatty phase | |
| Glycerol stearate and PEG-100 stearate | 1.2 g |
| PEG-20 stearate | 1.2 g |
| Stearic acid | 0.6 g |
| Cetyl alcohol | 1.2 g |
| Cetearyl octanoate and isopropyl myristate | 3 g |
| Caproyloylsalicylic acid | 1.5 g |
| Cyclomethicone | 7 g |
| PPG-3 myristyl ether | 7.5 g |
| Aqueous phase | |
| Crosslinked poly(2-acrylamido-2-methylpropanesulphonic acid) neutralized with ammonia, prepared according to the process of Preparation Example B, with a viscosity of the order of 7000 cPs in a 2% solution in water at 25° C. | 1.2 g AM |
| Kojic acid | 1 g |
| Caffeic acid | 0.2 g |
| PEG-8 | 15 g |
| Preservative q.s. | |
| Sterilized demineralized water q.s. for | 100 g |
| pH 3.1 | |

A smooth, white and, glossy cream was obtained.

What is claimed is:

1. A cosmetic or dermatological composition containing a cosmetically or dermatologically acceptable acidic aqueous medium and at least one crosslinked poly(2-acrylamido-2-methylpropanesulphonic acid) homopolymer neutralized to at least 90% which comprises, distributed randomly:

(a) from 90 to 99.9% by weight, relative to the weight of said at least one crosslinked homopolymer, of units of the following formula (1)

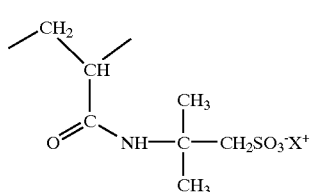

(1)

in which $X^+$ denotes a cation or a mixture of cations, it being possible for up to 10 mol % of the cations $X^+$ to be protons $H^+$; and (b) from 0.01 to 10% by weight, relative to the weight of said at least one crosslinked homopolymer, of crosslinking units originating from at least one monomer having at least two olefinic double bonds.

2. A composition according to claim 1, wherein said acidic aqueous medium has a pH less than or equal to 5.

3. A composition according to claim 2, wherein the pH of said acidic aqueous medium ranges from 1 to 4.

4. A composition according to claim 1, wherein said at least one crosslinked homopolymer contains a number of units of formula (1) in an amount which is sufficiently high to obtain a hydrodynamic volume of said homopolymer, in solution in water, having a radius ranging from 10 to 500 nm, with a homogeneous and unimodal distribution.

5. A composition according to claim 1, wherein said at least one crosslinked homopolymer contains from 98 to 99.5% by weight of units of formula (1) and from 0.2 to 2% by weight of crosslinking units.

6. A composition according to claim 1, wherein, in the formula (1), the cation $X^+$ is $NH_4^+$.

7. A composition according to claim 1, wherein said crosslinking units originating from at least one monomer correspond to the following formula (2):

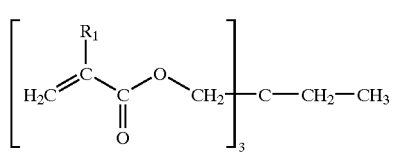

(2)

in which $R_1$ denotes a hydrogen atom or a $C_1$–$C_4$ alkyl radical.

8. A composition according to claim 1, wherein said at least one crosslinked homopolymer is crosslinked with trimethylolpropane triacrylate.

9. A composition according to claim 1, wherein said at least one crosslinked homopolymer exhibits a viscosity, measured with a Brookfield viscometer, rotor 4, at a rotational speed of 100 revolutions/minute in a 2% solution in water at 25° C., of greater than or equal to 1000 cPs.

10. A composition according to claim 9, wherein said at least one crosslinked homopolymer exhibits a viscosity ranging from 5000 to 40,000 cps.

11. A composition according to claim 10, wherein said at least one crosslinked homopolymer exhibits a viscosity ranging from 6500 to 35,000 cps.

12. A composition according to claim 1, wherein said at least one crosslinked homopolymer is present in a concentration ranging from 0.01 to 20% by weight with respect to the total weight of the composition.

13. A composition according to claim 1, wherein said at least one crosslinked homopolymer is present in a concentration ranging from 0.1 to 10% by weight with respect to the total weight of the composition.

14. A composition according to claim 1, wherein said cosmetically or dermatologically acceptable medium is water or water and at least one organic solvent selected from hydrophilic organic solvents, lipophilic organic solvents, and amphiphilic solvents.

15. A composition according to claim 14, wherein said at least one organic solvent is a mono- or polyfunctional alcohol, an oxyethylenated polyethylene glycol, a propylene glycol ester, sorbitol, a sorbitol derivative, a dialkyl isosorbide, a glycol ether, a propylene glycol ether, or a fatty ester.

16. A composition according to claim 14, wherein said at least one organic solvent represents from 5% to 98% of the total weight of the composition.

17. A composition according to claim 1, wherein said composition additionally comprises at least one fatty phase.

18. A composition according to claim 17, wherein said at least one fatty phase represents up to 50% of the total weight of the composition.

19. A composition according to claim 1, wherein said composition additionally comprises at least one cosmetically or dermatologically acceptable organic acid active principle.

20. A composition according to claim 19, wherein said organic acid active principle is ascorbic acid, kojic acid, citric acid, caffeic acid, salicylic acid or a derivative thereof, an α-hydroxy acid, mandelic acid, benzoic acid, phenyllactic acid, gluconic acid, galacturonicacid, aleuritic acid, ribonic acid, tartronic acid, tartaric acid, malic acid, fumaric acid, retinoic acid or a derivative thereof, benzene-1,4-di(3-methylidene-10-camphorsulphonic acid), urocanic acid, 2-phenylbenzimidazole-5-sulphonic acid, α-(2-oxo-3-bornylidene)toluene-4-sulphonic acid, 2-hydroxy4-methoxy-5-sulphonic acid, a plant extract containing acids, a derivative of acidic xanthine, β-glycyrrhetinic acid or asiatic acid.

21. A composition according to claim 20, wherein said organic acid active principle is a fruit extract.

22. A composition according to claim 1, wherein said composition additionally contains at least one additive selected from conventional hydrophilic or lipophilic gelling or thickening agents; hydrophilic or lipophilic active principles; preservatives; antioxidants; fragrances; emulsifiers; moisturizing agents; pigmenting agents; depigmenting agents; keratolytic agents; vitamins; emollients; sequestering agents; surfactants; polymers; basifying or acidifying agents; fillers; agents for combatting free radicals; ceramides; sunscreen agents; insect repellents; slimming agents; coloring materials; bactericides; and antidandruff agents.

23. A composition according to claim 22 wherein the sunscreen agents are ultraviolet screening agents.

24. A method for washing, caring for, conditioning or promoting form retention of the hairstyle or shaping the hair, said method comprising applying a composition according to claim 1 to the hair as a rinse-out or leave-in hair product.

25. A process for the non-therapeutic cosmetic treatment of skin, scalp, hair, eyelashes, eyebrows, nails or mucous membranes, wherein a composition according to claim 1 is applied on said skin, scalp, hair, eyelashes, eyebrows, nails or mucous membranes.

26. A process according to claim 25, wherein said composition is a care product, a hygiene product, a make-up product, or an anti-sun product.

27. A process for caring for and practicing hygiene of the mouth, said process comprising placing a composition having in an acidic aqueous medium at least one crosslinked poly(2-acrylamido-2-methylpropanesulphonic acid) polymer neutralized to at least 90% in the mouth as a toothpaste or mouthwash.

28. A non-therapeutic process for depigmenting human facial skin or human body skin, said process comprising applying a composition according to claim 1 to said skin.

29. A method for therapeutic treatment of human facial skin or human body skin, said method comprising applying to said skin a pomade or ointment containing an effective amount of the composition according to claim 1.

30. A method for gelling or thickening a cosmetic or dermatological composition containing an acidic aqueous medium, said method comprising adding, to said composition as a gelling or thickening agent, at least one crosslinked poly(2-acrylamido-2-methylpropanesulphonic acid)

homopolymer neutralized to at least 90% which comprises, distributed randomly:
(a) from 90 to 99.9% by weight, relative to the weight of said at least one crosslinked homopolymer, of units of the following formula (1)

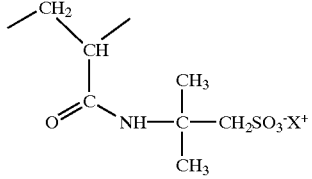

(1)

in which $X^+$ denotes a cation or a mixture of cations, it being possible for up to 10 mol % of the cations $X^+$ to be protons $H^+$; and
(b) from 0.01 to 10% by weight, relative to the weight of said at least one crosslinked homopolymer, of crosslinking units originating from at least one monomer having at least two olefinic double bonds.

31. A method for gelling or thickening a cosmetic or dermatological composition containing an aqueous medium rich in organic solvent, said method comprising adding, to said composition as a gelling or thickening agent, at least one crosslinked poly(2-acrylamido-2-methylpropanesulphonic acid) homopolymer neutralized to at least 90% which comprises, distributed randomly:
(a) from 90 to 99.9% by weight, relative to the weight of said at least one crosslinked homopolymer, of units of the following formula (1)

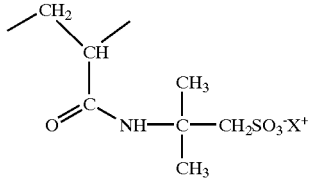

(1)

in which $X^+$ denotes a cation or a mixture of cations, it being possible for up to 10 mol % of the cations $X^+$ to be protons $H^+$; and
(b) from 0.01 to 10% by weight, relative to the weight of said at least one crosslinked homopolymer, of crosslinking units originating from at least one monomer having at least two olefinic double bonds.

32. A method for dissolving and stabilizing an organic acid active principle in a cosmetic or dermatological composition containing an acidic aqueous medium, said method comprising adding, to said composition as a gelling or thickening agent, at least one crosslinked poly(2-acrylamido-2-methylpropanesulphonic acid) homopolymer neutralized to at least 90% which comprises, distributed randomly:
(a) from 90 to 99.9% by weight, relative to the weight of said at least one crosslinked homopolymer, of units of the following formula (1)

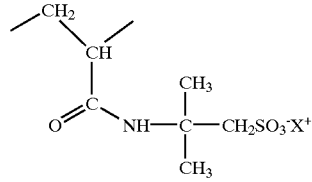

(1)

in which $X^+$ denotes a cation or a mixture of cations, it being possible for up to 10 mol % of the cations $X^+$ to be protons $H^+$; and
(b) from 0.01 to 10% by weight, relative to the weight of said at least one crosslinked homopolymer, of crosslinking units originating from at least one monomer having at least two olefinic double bonds.

33. A method for dissolving and stabilizing an organic acid active principle in a cosmetic or dermatological composition containing an aqueous medium rich in organic solvent, said method comprising adding, to said composition as a gelling or thickening agent, at least one crosslinked poly(2-acrylamido-2-methylpropanesulphonic acid) homopolymer neutralized to at least 90% which comprises, distributed randomly:
(a) from 90 to 99.9% by weight, relative to the weight of said at least one crosslinked homopolymer, of units of the following formula (1)

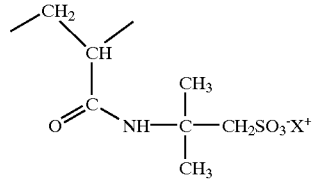

(1)

in which $X^+$ denotes a cation or a mixture of cations, it being possible for up to 10 mol % of the cations $X^+$ to be protons $H^+$; and
(b) from 0.01 to 10% by weight, relative to the weight of said at least one crosslinked homopolymer, of crosslinking units originating from at least one monomer having at least two olefinic double bonds.

* * * * *

UNITED STATES PATENT AND TRADEMARK OFFICE
CERTIFICATE OF CORRECTION

PATENT NO. : 6,468,549 B1  
DATED : October 22, 2002  
INVENTOR(S) : Dupuis et al.

It is certified that error appears in the above-identified patent and that said Letters Patent is hereby corrected as shown below:

<u>Title page,</u>  
Item [57], ABSTRACT,  
Line 4, "methylpropanesulfonic" should read -- methylpropanesulphonic --.

<u>Column 13,</u>  
Line 42, "cps" should read -- cPs --.  
Line 45, "cps" should read -- cPs --.

<u>Column 14,</u>  
Line 12, before "citric acid" delete the period.  
Line 14, "galacturonicacid" should read -- galacturonic acid --.  
Line 19, "2-hydroxy4-" should read -- 2-hydroxy-4- --.

Signed and Sealed this

Eighteenth Day of March, 2003

JAMES E. ROGAN  
*Director of the United States Patent and Trademark Office*